(12) United States Patent
Yi et al.

(10) Patent No.: US 10,213,179 B2
(45) Date of Patent: Feb. 26, 2019

(54) TOMOGRAPHY APPARATUS AND METHOD OF RECONSTRUCTING TOMOGRAPHY IMAGE

(71) Applicant: Samsung Electronics Co., Ltd, Gyeonggi-do (KR)

(72) Inventors: Jong-hyon Yi, Gyeonggi-do (KR); Toshihiro Rifu, Gyeonggi-do (KR); Ajay Narayanan, Gyeonggi-do (KR); Alexander Zamyatin, Gyeonggi-do (KR); Seok-min Han, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 68 days.

(21) Appl. No.: 15/415,805

(22) Filed: Jan. 25, 2017

(65) Prior Publication Data

US 2017/0209112 A1 Jul. 27, 2017

(30) Foreign Application Priority Data

Jan. 25, 2016 (KR) .................. 10-2016-0008891

(51) Int. Cl.
| | |
|---|---|
| *G06K 9/00* | (2006.01) |
| *A61B 6/00* | (2006.01) |
| *G06T 11/00* | (2006.01) |
| *A61B 6/03* | (2006.01) |
| *A61B 5/00* | (2006.01) |

(52) U.S. Cl.
CPC ............ *A61B 6/5264* (2013.01); *A61B 5/721* (2013.01); *A61B 6/032* (2013.01); *A61B 6/037* (2013.01); *G06T 11/003* (2013.01); *G06T 11/008* (2013.01); *A61B 5/0066* (2013.01)

(58) Field of Classification Search
CPC ......... A61B 5/721; A61B 6/032; A61B 6/037; A61B 5/0066; A61B 6/5264
USPC .............. 378/4, 901; 600/407, 425; 382/131
See application file for complete search history.

(56) References Cited

U.S. PATENT DOCUMENTS

| | | | |
|---|---|---|---|
| 6,236,704 B1 | 5/2001 | Navab et al. | |
| 7,492,967 B2 | 2/2009 | Toki et al. | |
| 7,840,249 B2* | 11/2010 | Wang ..................... | A61B 6/032 378/4 |
| 7,953,263 B2 | 5/2011 | Okamoto et al. | |
| 2010/0121183 A1 | 5/2010 | Taguchi et al. | |
| 2013/0077843 A1 | 3/2013 | Bruder et al. | |
| 2015/0243070 A1* | 8/2015 | Ra ......................... | A61B 6/503 382/131 |

FOREIGN PATENT DOCUMENTS

| | | |
|---|---|---|
| DE | 102013200163 B4 | 9/2014 |
| JP | 2000051197 | 2/2000 |
| JP | 4519434 B2 | 8/2010 |

\* cited by examiner

*Primary Examiner* — Charlotte M Baker

(57) ABSTRACT

Provided are a tomography apparatus and a method for reconstructing a tomography image. The method includes obtaining a plurality of raw data corresponding to a plurality of views by performing a tomography scan on an object and deblurring each of the plurality of raw data based on a point spread function (PSF) that varies according to locations in a field of view (FOV) in a gantry. The method also includes reconstructing a final tomography image in which a motion of the object is corrected from the plurality of deblurred raw data based on a motion vector indicating the motion of the object.

13 Claims, 8 Drawing Sheets

TOMOGRAPHY APPARATUS AND METHOD OF RECONSTRUCTING TOMOGRAPHY IMAGE

CROSS-REFERENCE TO RELATED APPLICATION(S) AND CLAIM OF PRIORITY

The present application is related to and claims the benefit of Korean Patent Application No. 10-2016-0008891, filed on Jan. 25, 2016, in the Korean Intellectual Property Office, the disclosure of which is incorporated herein in its entirety by reference.

TECHNICAL FIELD

The present disclosure relates to tomography apparatuses and methods, performed by the tomography apparatuses, of reconstructing tomography images, and more particularly, to methods, performed by the tomography apparatuses, of reconstructing tomography images, in which a resolution of medical tomography images may be improved.

BACKGROUND

Medical imaging apparatuses are used to obtain an image of an internal structure of an object. Medical imaging apparatuses that are non-invasive testing apparatuses capture images and provide a processed image to a user including processed structural details, internal tissues, and the flow of fluids in a human body. The user, who is, for example, a medical doctor, may diagnose a health state and a disease of a patient by using a medical image output from a medical image processing apparatus.

A computed tomography (CT) apparatus is a typical apparatus among apparatuses for capturing an image of an object by projecting X-rays to a patient.

Among medical image processing apparatuses, the CT apparatus may provide a cross-sectional image of an object that may show an internal structure (e.g., organs such as kidneys or lungs) of the object without overlapping elements in the internal structure, compared to a general X-ray apparatus. Therefore, the tomography apparatus is widely used for accurate diagnosis of diseases. Hereinafter, a medical image obtained by the apparatus is referred to as a tomography image.

To obtain a tomography image, a tomography scan is performed on the object by using a tomography apparatus, and thus raw data is obtained. Then, the tomography image is reconstructed by using the obtained raw data. The raw data may be projection data, which is obtained by projecting X-rays to the object, or a sinogram that is a group of pieces of the projection data.

Due to movement of a tomography apparatus or an object to be scanned or due to performance of the tomography apparatus, blurring artifacts may occur when reconstructing a tomography image. For example, the tomography apparatus itself may undergo shaking during an operation, resulting in blurring artifacts in an image.

When blurring artifacts occurs, an outermost edge of the object may be unclear. Also, an inner edge of the CT image may be blurred due to blurring artifacts.

In addition, if an object to be scanned moves, movement of the object may also occur within one period, causing motion artifacts when reconstructing a CT image.

As described above, blurring artifacts and motion artifacts in a CT image may decrease the quality of the CT image, and thus hinder the ability of the user, such as a medical doctor, to accurately read the CT image and diagnose diseases.

Therefore, in tomography, blurring artifacts and motion artifacts of a tomography image need to be minimized.

SUMMARY

To address the above-discussed deficiencies, it is a primary object to provide Provided are tomography apparatuses and methods, performed by the tomography apparatuses, of reconstructing tomography images, in which blurring artifacts and motion artifacts of a tomography image may be reduced.

Additional aspects will be set forth in part in the description which follows and, in part, will be apparent from the description, or may be learned by practice of the presented embodiments.

According to an aspect of an embodiment, a method of reconstructing a tomography image, includes: obtaining a plurality of raw data respectively corresponding to a plurality of views by performing a tomography scan on an object; deblurring the plurality of raw data, based on a point spread function (PSF) that varies according to locations in a field of view (FOV) in a gantry; and reconstructing a final tomography image in which a motion of the object is corrected from the plurality of deblurred raw data, based on a motion vector indicating the motion of the object.

The deblurring may include deconvoluting the raw data based on the PSF that varies according to the locations in the FOV in the gantry.

The method may further include: obtaining a plurality of partial images by using the plurality of raw data respectively corresponding to different views obtained by performing a tomography scan on the object; measuring a motion of the object based on the plurality of partial images; and representing the measured motion of the object as the motion vector.

The method may further include estimating a PSF that varies according to the locations in the FOV in the gantry corresponding to the plurality of views, based on the plurality of raw data.

According to an aspect of another embodiment, a method of reconstructing a tomography image, includes: obtaining a plurality of raw data respectively corresponding to a plurality of views by performing a tomography scan on an object; calculating time points respectively corresponding to the plurality of views; correcting locations of all voxels that construct a field of view (FOV) in a gantry, based on a motion vector corresponding to each of the time points; and deblurring the plurality of raw data based on a point spread function (PSF) corresponding to the corrected locations of the voxels.

The deblurring may include estimating the PSF corresponding to locations of the voxels based on angles corresponding to the views and the corrected locations of the voxels.

The deblurring may further include: calculating projection coordinates corresponding to the corrected locations of the voxels; and deconvoluting the projection coordinates based on the PSF corresponding to the corrected locations of the voxels.

The method may further include: predicting in advance a motion in each of the voxels, with respect to the time points respectively corresponding to the plurality of views, and representing the predicted motion as each of the motion vectors; and storing each of the motion vectors.

The method may further include reconstructing a final tomography image based on the plurality of deblurred raw data.

According to an aspect of another embodiment, a tomography apparatus includes: a data obtainer configured to obtain a plurality of raw data respectively corresponding to a plurality of views by performing a tomography scan on an object; and an image processor configured to deblur the plurality of raw data, based on a point spread function (PSF) varying according to locations in a field of view (FOV) in a gantry, and reconstruct a final tomography image in which a motion of the object is corrected from the plurality of deblurred raw data, based on a motion vector indicating the motion of the object.

The image processor may deconvolute the plurality of raw data based on the PSF varying according to the locations in the FOV in the gantry.

The data obtainer may obtain a plurality of partial images by using the plurality of raw data respectively corresponding to different views obtained by performing a tomography scan on an object, wherein the image processor measures a motion of the object based on the plurality of partial images and represents the measured motion of the object as the motion vector.

The image processor may estimate a PSF corresponding to the plurality of views and varying according to the locations in the FOV in the gantry, based on the plurality of raw data.

According to an aspect of another embodiment, a tomography apparatus includes: a data obtainer configured to obtain a plurality of raw data respectively corresponding to a plurality of views by performing a tomography scan on an object; and an image processor configured to calculate time points respectively corresponding to the plurality of views and correct locations of all voxels that construct a field of view (FOV) in a gantry, based on a motion vector corresponding to each of the time points, and deblur the plurality of raw data based on a point spread function (PSF) corresponding to the corrected locations of the voxels.

The image processor may estimate the PSF corresponding to locations of the voxels based on angles corresponding to the views and the corrected locations of the voxels.

The image processor may calculate projection coordinates corresponding to the corrected locations of the voxels, and deconvolute the projection coordinates based on the PSF corresponding to the corrected locations of the voxels.

The tomography apparatus may further include a memory, wherein the image processor predicts in advance a motion in each voxel with respect to time points respectively corresponding to the plurality of views, and representing the predicted motion as each of the motion vectors, wherein the memory stores each of the motion vectors.

The image processor may reconstruct a final tomography image based on the plurality of deblurred raw data.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts: These and/or other aspects will become apparent and more readily appreciated from the following description of the embodiments, taken in conjunction with the accompanying drawings in which.

DETAILED DESCRIPTION

Figure 1:
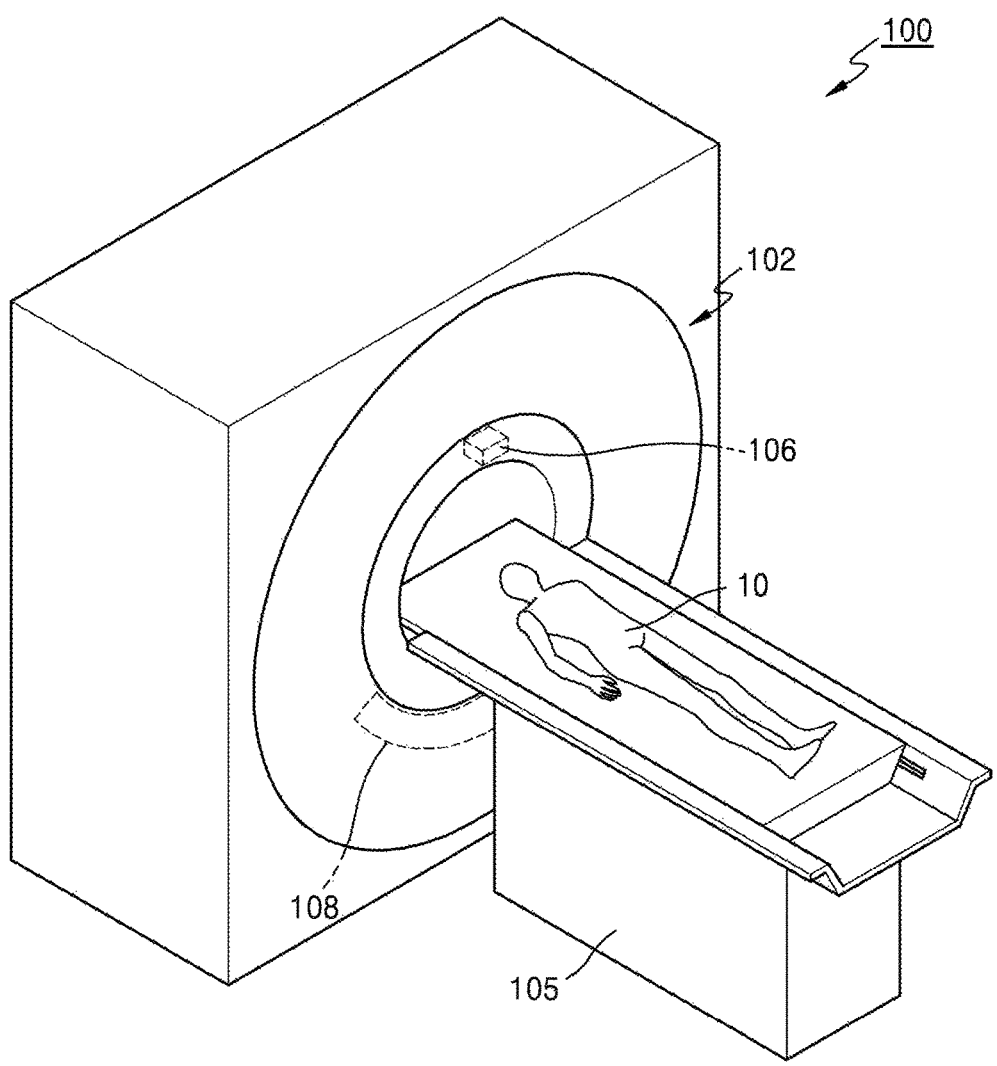
FIG. 1 illustrates a schematic diagram of a general computed tomography (CT) system.

FIGS. 1 through 9B, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged tomography device.

As used herein, the term "and/or" includes any and all combinations of one or more of the associated listed items. Expressions such as "at least one of," when preceding a list of elements, modify the entire list of elements and do not modify the individual elements of the list.

Advantages and features of one or more exemplary embodiments and methods for accomplishing the same may be understood more readily by reference to the following detailed description of the exemplary embodiments and the accompanying drawings. In this regard, the present exemplary embodiments may have different forms and should not be construed as being limited to the descriptions set forth herein. Rather, these exemplary embodiments are provided so that this disclosure will be thorough and complete and will fully convey the concept of the present exemplary embodiments to one of ordinary skill in the art, and the present inventive concept will only be defined by the appended claims Like reference numerals refer to like elements throughout the specification.

Hereinafter, the terms used in the specification will be briefly defined, and the exemplary embodiments will be described in detail.

All terms including descriptive or technical terms which are used herein should be construed as having meanings that are well-known to one of ordinary skill in the art. However, the terms may have different meanings according to the intention of one of ordinary skill in the art, precedent cases, or the appearance of new technologies. Also, some terms may be arbitrarily selected by the applicant, and in this case, the meaning of the selected terms will be described in detail in the detailed description. Thus, the terms used herein have to be defined based on the meaning of the terms together with the description throughout the specification.

When a part "includes or comprises" an element, unless there is a particular description contrary thereto, the part can further include other elements, not excluding the other elements. Also, the term "unit" in the exemplary embodiments refers to a software component or a hardware component such as a field-programmable gate array (FPGA) or an application-specific integrated circuit (ASIC), and performs a specific function. However, the term "unit" is not limited to software or hardware. The "unit" may be formed so as to be in an addressable storage medium, or may be formed so as to operate one or more processors. Thus, for example, the term "unit" may refer to components such as software components, object-oriented software components, class components, and task components, and may include processes, functions, attributes, procedures, subroutines, segments of program code, drivers, firmware, micro codes, circuits, data, a database, data structures, tables, arrays, and/or variables. A function provided by the components and "units" may be associated with the smaller number of components and units, or may be divided into additional components and "units".

It will be understood that the terms "comprises" and/or "comprising" used herein specify the presence of stated features or components, but do not preclude the presence or addition of one or more other features or components. In addition, the terms such as "unit," "-er (-or)," and "module" described in the specification refer to an element for performing at least one function or operation, and may be implemented in hardware, software, or the combination of hardware and software.

Reference will now be made in detail to exemplary embodiments, examples of which are illustrated in the accompanying drawings, wherein like reference numerals refer to the like elements throughout. In this regard, the present exemplary embodiments may have different forms and should not be construed as being limited to the descriptions set forth herein. In the following description, well-known functions or constructions are not described in detail so as not to obscure the exemplary embodiments with unnecessary detail.

Throughout the specification, an "image" may mean multi-dimensional data formed of discrete image elements, e.g., pixels in a two-dimensional (2D) image and voxels in a three-dimensional (3D) image. For example, the image may include a medical image of an object that is captured using a tomography apparatus.

Throughout the specification, a "computed tomography (CT) image" may mean an image generated by synthesizing a plurality of X-ray images that are obtained by capturing an image of an object while a tomography apparatus rotates around at least one axis with respect to the object.

Throughout the specification, examples of an "object" may include a human, an animal, or a part of a human or animal. For example, examples of the object may include at least one of organs such as liver, heart, womb, brain, breast, abdomen, etc., and blood vessels. Also, the "object" may include a phantom. The phantom means a material having a volume that is very close to a density and effective atomic number of an organism, and may include a sphere phantom having a characteristic similar to a physical body.

Throughout the specification, a "user" may be, but is not limited to, a medical expert including a doctor, a nurse, a medical laboratory technologist, a medial image expert, and a technician who repairs a medical apparatus.

As a CT system is capable of providing a cross-sectional image of an object, the CT system may express an inner structure (e.g., organs such as kidneys or lungs) of the object without an overlap therebetween, contrary to a general X-ray imaging apparatus.

In detail, a tomography system may include all tomography apparatuses such as a CT apparatus, an optical coherence tomography (OCT) apparatus, or a positron emission tomography (PET)-CT apparatus.

In the following description, a CT system is exemplified as the tomography system.

The CT system may obtain a plurality of pieces of image data with a thickness of not more than 2 mm, several hundreds of times per second, and then may process the plurality of pieces of image data, so that the CT system may provide a relatively accurate cross-sectional image of the object. According to the related art, only a horizontal cross-sectional image of the object can be obtained, but this issue has been overcome due to various image reconstruction methods. Examples of 3D image reconstruction methods are as below:

Shade surface display (SSD)—an initial 3D imaging method that displays only voxels having a predetermined Hounsfield Unit (HU) value.

Maximum intensity projection (MIP)/minimum intensity projection (MinIP)—a 3D imaging method that displays only voxels having the greatest or smallest HU value among voxels that construct an image.

Volume rendering (VR)—an imaging method capable of adjusting a color and transmittance of voxels that construct an image, according to regions of interest.

Virtual endoscopy—a method that allows an endoscopy observation in a 3D image that is reconstructed using the VR method or the SSD method.

Multi-planar reformation (MPR)—a method used to reconstruct an image into a different cross-sectional image. A user may reconstruct an image in every desired direction.

Editing—a method that involves editing adjacent voxels to allow a user to easily observe a region of interest in volume rendering.

Voxel of interest (VOI)—a method that displays only a selected area in volume rendering.

A CT system 100 according to an exemplary embodiment will now be described with reference to FIG. 1. The CT system 100 may include various types of devices.

FIG. 1 illustrates a schematic diagram of the CT system 100 according to an exemplary embodiment. Referring to FIG. 1, the CT system 100 may include a gantry 102, a table 105, an X-ray generator 106, and an X-ray detector 108.

The gantry 102 may include the X-ray generator 106 and the X-ray detector 108.

An object 10 may be positioned on the table 105.

The table 105 may move in a predetermined direction, for example, at least one of up, down, right, and left directions, during a CT scan process. Also, the table 105 may tilt or rotate by a predetermined degree in a predetermined direction.

The gantry 102 may also tilt by a predetermined degree in a predetermined direction.

Figure 2:
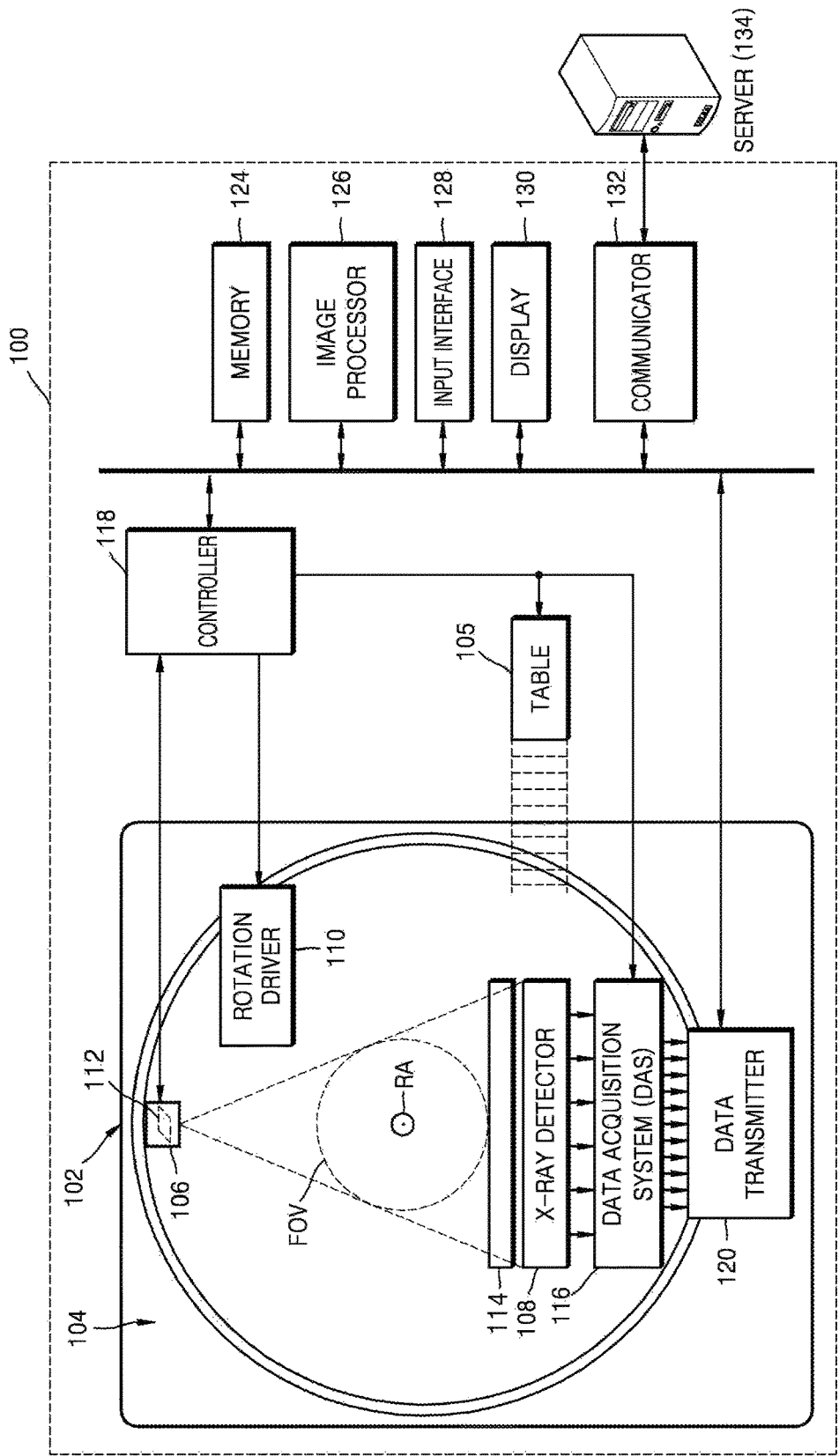
FIG. 2 illustrates a structural block diagram of a CT system according to an exemplary embodiment.

FIG. 2 illustrates a structural block diagram of the CT system 100.

The CT system 100 may include the gantry 102, the table 105, a controller 118, a memory 124, an image processor 126, an input interface 128, a display 130, and a communicator 132.

As described above, the object 10 may be positioned on the table 105. In an exemplary embodiment, the table 105 may move in a predetermined direction, for example, at least one of up, down, right, and left directions, and motion of the table 105 may be controlled by the controller 118.

The gantry 102 may include a rotating frame 104, the X-ray generator 106, the X-ray detector 108, a rotation driver 110, a data acquisition system (DAS) 116, and a data transmitter 120.

The gantry 102 may include the rotating frame 104 having a loop shape capable of rotating with respect to a predetermined rotation axis RA. The rotating frame 104 may also have a disc shape.

The rotating frame 104 may include the X-ray generator 106 and the X-ray detector 108 that are arranged to face each other to have predetermined fields of view (FOV). The rotating frame 104 may also include an anti-scatter grid 114. The anti-scatter grid 114 may be positioned between the X-ray generator 106 and the X-ray detector 108.

In a medical imaging system, X-ray radiation that reaches a detector (or a photosensitive film) includes not only attenuated primary radiation that forms a valuable image but also scattered radiation that deteriorates the quality of an image. To transmit most of the primary radiation and to attenuate the scattered radiation, the anti-scatter grid 114 may be positioned between a patient and the detector (or the photosensitive film).

For example, the anti-scatter grid 114 may be formed by alternately stacking lead foil strips and an interspace material such as a solid polymer material, solid polymer, or a fiber composite material. However, formation of the anti-scatter grid 114 is not limited thereto.

The rotating frame 104 may receive a driving signal from the rotation driver 110 and may rotate the X-ray generator 106 and the X-ray detector 108 at a predetermined rotation speed. The rotating frame 104 may receive the driving signal and power from the rotation driver 110 while the rotating frame 104 contacts the rotation driver 110 via a slip ring. Also, the rotating frame 104 may receive the driving signal and power from the rotation driver 110 via wireless communication.

The X-ray generator 106 may receive a voltage and current from a power distribution unit (PDU) via a slip ring (not shown) and a high voltage generator (not shown), and then may generate and project X-rays. When the high voltage generator applies predetermined voltage (hereinafter, referred to as the tube voltage) to the X-ray generator 106, the X-ray generator 106 may generate X-rays having a plurality of energy spectra that correspond to the tube voltage.

The X-rays generated by the X-ray generator 106 may be emitted in a predetermined form via a collimator 112.

The X-ray detector 108 is positioned to face the X-ray generator 106. The X-ray detector 108 may include a plurality of X-ray detectors. Each of the plurality of X-ray detectors may establish one channel, but one or more exemplary embodiments are not limited thereto.

The X-ray detector 108 may detect the X-ray that is generated by the X-ray generator 106 and that is transmitted through the object 10, and may generate an electrical signal corresponding to intensity of the detected X-ray.

The X-ray detector 108 may include an indirect-type X-ray detector for detecting radiation after converting the radiation into light, and a direct-type X-ray detector for detecting radiation after directly converting the radiation into electric charges. The indirect-type X-ray detector may use a scintillator. Also, the direct-type X-ray detector may use a photon counting detector. The DAS 116 may be connected to the X-ray detector 108. The electrical signal generated by the X-ray detector 108 may be collected by the DAS 116 in a wired or wireless manner. Also, the electrical signal generated by the X-ray detector 108 may be provided to an analog-to-digital converter (ADC) (not shown) via an amplifier (not shown).

According to a slice thickness or the number of slices, only part of data collected by the X-ray detector 108 may be provided to the image processor 126, or the image processor 126 may select only part of data.

The digital signal may be provided to the image processor 126 via the data transmitter 120. The digital signal may be transmitted to the image processor 126 via the data transmitter 120 in a wired or wireless manner.

The controller 118 according to the exemplary embodiment may control an operation of each of modules in the CT system 100. For example, the controller 118 may control operations of the table 105, the rotation driver 110, the collimator 112, the DAS 116, the memory 124, the image processor 126, the input interface 128, the display 130, the communicator 132, or the like.

The image processor 126 may receive data, for example, raw data before being processed, which is obtained from the DAS 116, via the data transmitter 120, and may perform pre-processing.

The pre-processing may include a process of correcting sensitivity irregularity between channels and a process of correcting signal loss due to a rapid decrease of signal strength or due to an X-ray absorbing material such as metal.

Data output from the image processor 126 may be referred to as raw data or projection data. The projection data may be stored in the memory 124 along with information about imaging conditions, for example, the tube voltage, an imaging angle, etc., during the acquisition of data.

The projection data may be a group of data values that correspond to the intensity of the X-ray that passes through the object 10. For convenience of description, a group of a plurality of pieces of projection data that are simultaneously obtained from all channels at the same imaging degree will be referred to as a projection data set.

The memory 124 may include at least one storage medium among a flash memory-type storage medium, a hard disk-type storage medium, a multimedia card micro-type storage medium, card-type memories such as an SD card, an XD memory, etc., random access memory (RAM), static random access memory (SRAM), read-only memory (ROM), electrically erasable programmable ROM (EEPROM), programmable ROM (PROM), magnetic memory, a magnetic disc, and an optical disc.

The image processor 126 may reconstruct a cross-sectional image with respect to the object 10 by using the obtained projection data set. The cross-sectional image may be a 3D image. In other words, the image processor 126 may reconstruct a 3D image of the object 10 by using, for example, a cone beam reconstruction method based on the obtained projection data set.

The input interface 128 may receive an external input with respect to an X-ray tomography imaging condition, an image processing condition, etc. For example, the X-ray tomography imaging condition may include tube voltages, an energy value setting with respect to a plurality of X-ray beams, selection of an imaging protocol, selection of an image reconstruction method, a setting of a FOV area, the number of slices, a slice thickness, a parameter setting with respect to image post-processing, etc. Also, the image processing condition may include a resolution of an image, an attenuation coefficient setting with respect to the image, a setting of an image combining ratio, etc.

The input interface 128 may include a device for receiving a predetermined input from an external source. For example, the input interface 128 may include a microphone, a keyboard, a mouse, a joystick, a touchpad, a touch pen, a voice recognition device, a gesture recognition device, etc.

The display 130 may display an X-ray image reconstructed by the image processor 126.

Exchanges of data, power, etc. between the aforementioned elements may be performed using at least one of wired communication, wireless communication, and optical communication.

The communicator 132 may perform communication with an external device, an external medical apparatus, etc. via a server 134, etc. The communication will now be described with reference to FIG. 3.

Figure 3:
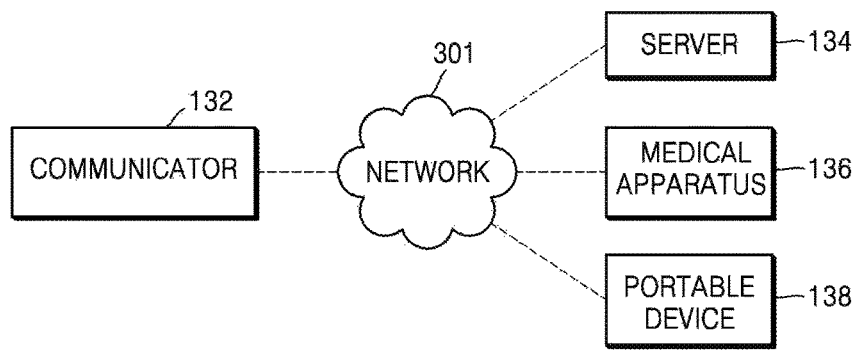
FIG. 3 illustrates a structural block diagram of a communicator.

FIG. 3 illustrates a block diagram of the communicator 132.

The communicator 132 may be connected to a network 301 in a wired or wireless manner and therefore may perform communication with the server 134, an external medical apparatus 136, or an external portable device 138. The communicator 132 may exchange data with a hospital server or other medical apparatuses in a hospital connected via a picture archiving and communication system (PACS).

The communicator 132 may perform data communication with the external portable device 138 or the like according to a digital imaging and communications in medicine (DICOM) standard.

The communicator 132 may transmit and receive data related to diagnosing the object 10, via the network 301. Also, the communicator 132 may transmit and receive a medical image obtained from the external medical apparatus 136 such as a magnetic resonance imaging (MRI) apparatus, an X-ray apparatus, etc.

Furthermore, the communicator 132 may receive a diagnosis history or a medical treatment schedule about a patient from the server 134, and may use the diagnosis history or the medical treatment schedule in a clinical diagnosis for the patient. Also, the communicator 132 may perform data communication not only with the server 134 or the external medical apparatus 136 in a hospital but also with the external portable device 138 of a user or patient.

Also, the communicator 132 may transmit information about a device error, information about a quality control status, etc. to a system manager or a service manager via the network 301, and may receive feedback corresponding to the information.

All imaging apparatuses have a spatial resolution that indicates an accuracy of an image formed by capturing an object in a space. Due to unique characteristics of the imaging apparatuses, the imaging apparatuses cannot obtain perfect images of an object at a captured time point without blurring. That is, shaking of the imaging apparatuses that may occur during operation of the imaging apparatuses may cause shake effects in captured images as well. In addition, if an object undergoing tomography shakes, the movement of the object may result in blurring in a captured image.

The spatial resolution is determined according to a degree of blur in a processed image. For example, an image captured by an imaging apparatus with a high spatial resolution is less blurry than that captured by an imaging apparatus with a low spatial resolution.

A tomography apparatus also has a spatial resolution. The spatial resolution may be affected by tomography performance and motion of an object. For example, blurring artifacts generated due to a limitation in performance of a tomography apparatus and motion artifacts generated due to motion of an object may occur. The blurring artifacts and the motion artifacts in a tomography image may decrease the quality of the tomography image and thus hinder the ability of the user, such as a medical doctor, to accurately read the tomography image and diagnose diseases. For example, if blurring artifacts are generated in a portion of an image showing a calcified region, blood vessels which are in fact not blocked may seem as though they are blocked, and this may decrease an accuracy of diagnosing vascular diseases.

The blurring artifacts may be reduced by estimating a point spread function (PSF) and de-blurring images based on the PSF. The PSF varies according to tomography apparatuses, specifically, according to product specifications and/or performance of the tomography apparatuses. The PSF has a complicated structure, and may vary according to a location of a field of view (FOV) in a gantry and a tube current measured in milliamperes for generating X-rays. Correction of the blurring artifacts may be referred to as de-blurring or de-blooming. Hereinafter, correction of blurring artifacts will be referred to as deblurring.

In addition, motion artifacts may be reduced by acquiring raw data with a minimized duration or an angle corresponding to one period. A 'period' refers to a duration or an angle (phase) during which or at which the X-ray generator 106 rotates to acquire raw data needed to reconstruct a tomography image.

With regard to a reconstruction of a tomography image, reconstructing a tomography image by using raw data that is obtained as the X-ray generator 106 rotates a half turn or more and less than one turn is referred to a half reconstruction method, and reconstructing a tomography image by using raw data that is obtained as the X-ray generator 106 rotates one full turn is referred to as a full reconstruction method. In the half reconstruction method, an angle section in which the X-ray generator 106 rotates is smaller than that of the full reconstruction method, and thus a tomography image reconstructed using the half reconstruction method may have less motion artifacts than a tomography image obtained using the full reconstruction method.

Figure 4:
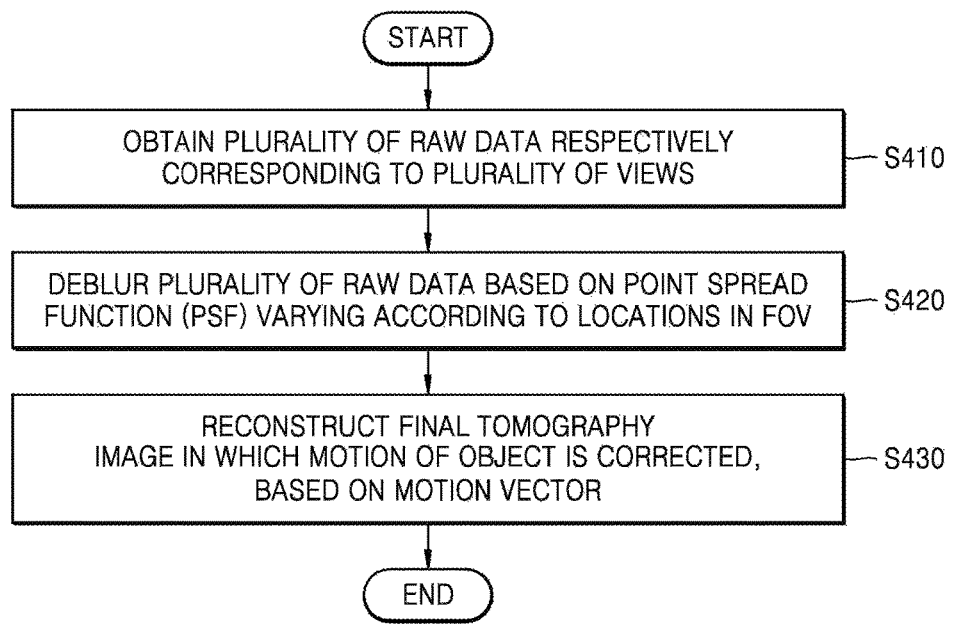
FIG. 4 illustrates a flowchart of a method of reconstructing a tomography image, according to an exemplary embodiment.

FIG. 4 illustrates a flowchart of a method of reconstructing a tomography image according to an exemplary embodiment.

In operation S410, the tomography apparatus obtains a plurality of raw data respectively corresponding to a plurality of views by performing a tomography scan on an object.

In operation S420, the tomography apparatus deblurs the plurality of raw data based on a PSF varying according to locations in a field of view FOV in a gantry.

The object may include a predetermined organ. In detail, the object may include at least one selected from among the heart, the abdomen, the womb, the brain, breasts, and the liver. For example, the object may include the heart that is expressed by a surface thereof. The heart may include at least one of tissues having different brightness values in a predetermined area.

When the X-ray generator 106 at a predetermined position projects X-rays to the object, a viewpoint or a direction in which the X-ray generator 106 faces the object is referred to as a 'view.' The raw data may be projection data obtained by projecting X-rays to the object, or a sinogram that is a collection of pieces of the projection data. In addition, the raw data may be an image generated by performing filtered backprojection on a sinogram. The projection data is raw data that is obtained with respect to a view, and the sinogram is raw data that is obtained by sequentially listing a plurality of pieces of projection data.

The tomography apparatus may deconvolute the plurality of raw data based on a PSF varying according to locations in a FOV.

The PSF may vary according to locations in a FOV in a gantry. If the plurality of raw data is deblurred based on a single PSF in every location in a FOV, an inaccurate PSF may be applied to some locations. However, according to the exemplary embodiment, the tomography apparatus may deblur the plurality of raw data based on a PSF varying according to locations in a FOV in a gantry, thereby applying accurate PSFs corresponding to respective locations.

The PSF according to each location may be estimated in the form of a Gaussian function, but one or more exemplary embodiments are not limited thereto. In addition, according to an embodiment, the tomography apparatus may estimate a PSF according to each location in advance and store the PSF, and perform deblurring the plurality of raw data based on the stored PSF when taking an image of an object. In addition, the tomography apparatus may retrieve a PSF varying according to locations in a FOV in a gantry, from an external device.

In operation S430, the tomography apparatus may reconstruct a final tomography image in which motion of the object is corrected, from the plurality of deblurred raw data, based on a motion vector indicating a motion of the object.

The longer a rotation of the gantry takes to obtain a plurality of raw data needed to reconstruct an image, the greater the amount of motion artifacts. Thus, the tomography apparatus may calculate a motion vector indicating a motion of the object based on a plurality of partial images obtained by performing a tomography scan on each of different angular sections that are less than 180 degrees. The partial images will be described below with reference to FIG. 5.

The tomography apparatus may calculate a motion vector in advance and store the motion vector in advance before capturing an image of an object. Accordingly, the tomography apparatus may correct a motion of the object based on the motion vector.

Figure 5:
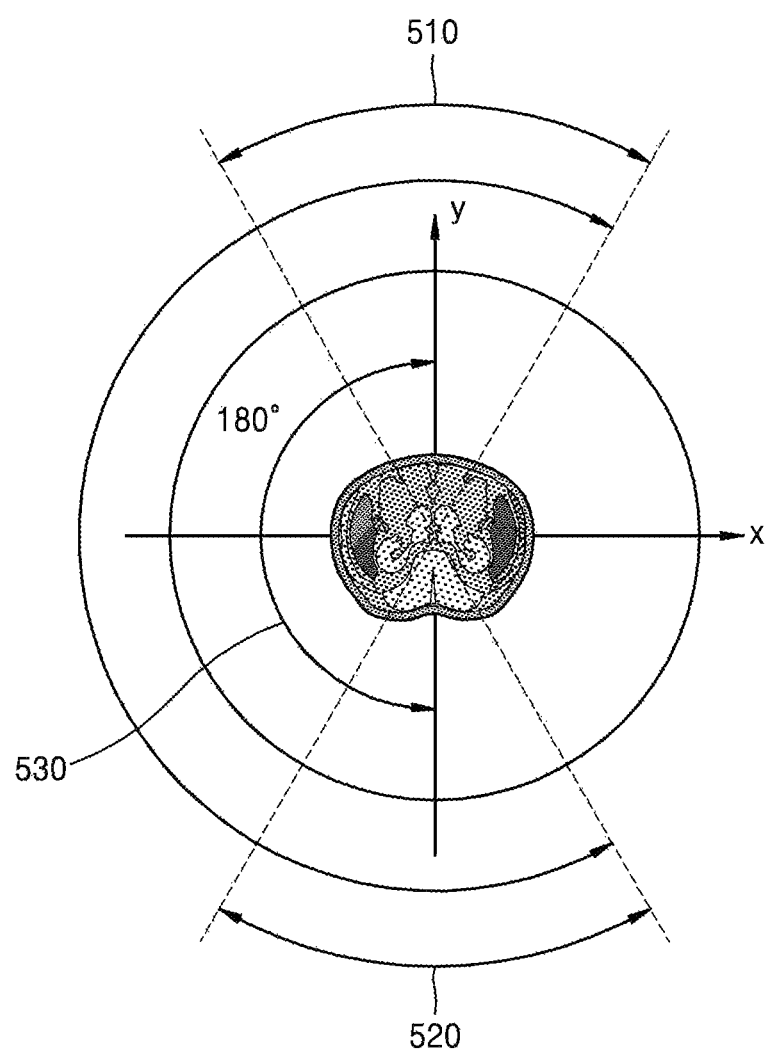
FIG. 5 illustrates a diagram for describing a partial image according to an exemplary embodiment.

FIG. 5 illustrates a diagram for describing a partial image according to an exemplary embodiment.

As described above, the tomography apparatus may calculate a motion vector indicating a motion of an object based on a plurality of partial images obtained by performing a tomography scan on first and second angular sections 510 and 520 that are different from each other and have an angle of less than 180 degrees.

For example, the tomography apparatus may obtain raw data by performing a tomography scan on each of the first angular section 510 and the second angular section 520 each having an angle of less than 180 degrees, and obtain a first image and a second image based on the raw data. The first angular section 510 and the second angular section 520 are included in an angular section within a period, and may have a conjugate angle relationship therebetween.

The first image and the second image may be reconstructed using a partial angle reconstruction (PAR) method. As the first image and the second image are reconstructed based on the raw data obtained in an angular section of less than 180 degrees, they may be not complete images that show the entire object but incomplete images that show only a part of the object. An incomplete image showing a part of an object like the first and second images may be referred to as a 'partial image' or a 'partial angle image.'

In addition, when the first angular section 510 and the second angular section 520 have a conjugate angle relationship therebetween, views of the first and second angular sections 510 and 520 are the same, and thus, the first and second images display a boundary of the same part of the object. Accordingly, by comparing the first and second images, the tomography apparatus may determine a difference between surfaces of the same part of the object included in the first and second images and determine a degree of a motion of the object. Then the tomography apparatus may calculate a motion vector indicating the motion of the object based on the first and second images. The motion vector may indicate a difference in at least one of a shape, size, and position between a predetermined object included in the first image and a predetermined object included in the second image, that occurs due to the motion of the object.

Figure 6:
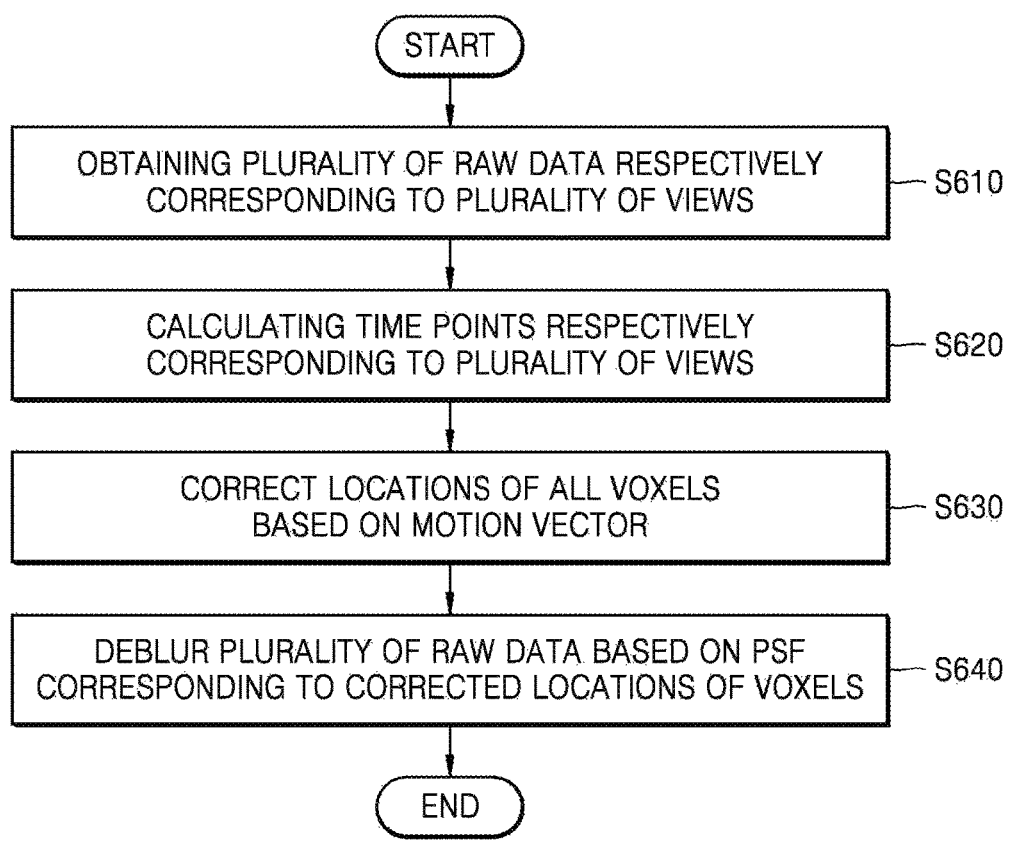
FIG. 6 illustrates a flowchart of a method of reconstructing a tomography image, according to another exemplary embodiment.

FIG. 6 illustrates a flowchart of a method of reconstructing a tomography image according to another exemplary embodiment.

In operation S610, the tomography apparatus obtains a plurality of raw data respectively corresponding to a plurality of views by performing a tomography scan on an object.

In operation S620, the tomography apparatus calculates time points respectively corresponding to the plurality of views.

In operation S630, the tomography apparatus corrects locations of voxels that construct a field of view formed in a gantry, based on a motion vector corresponding to each time point.

Motion of the object is different over time, and thus a motion vector indicating the motion of the object also varies over time. Accordingly, the tomography apparatus may calculate time points respectively corresponding to the views when correcting the motion of the object, and may correct the motion of the object by applying a motion vector corresponding to the calculated time point.

The motion vector will be further described with reference to FIG. 7 below.

In operation S640, the tomography apparatus may perform deblurring the plurality of raw data based on a PSF corresponding the corrected locations of the voxels. The corrected locations of the voxels may be locations of the voxels in which a motion of the object is corrected at a predetermined time point. Accordingly, the tomography apparatus may perform deblurring the plurality of raw data based on an accurate PSF by applying a PSF that corresponds to the locations of voxels in which the motion of the object is corrected.

Figure 7:
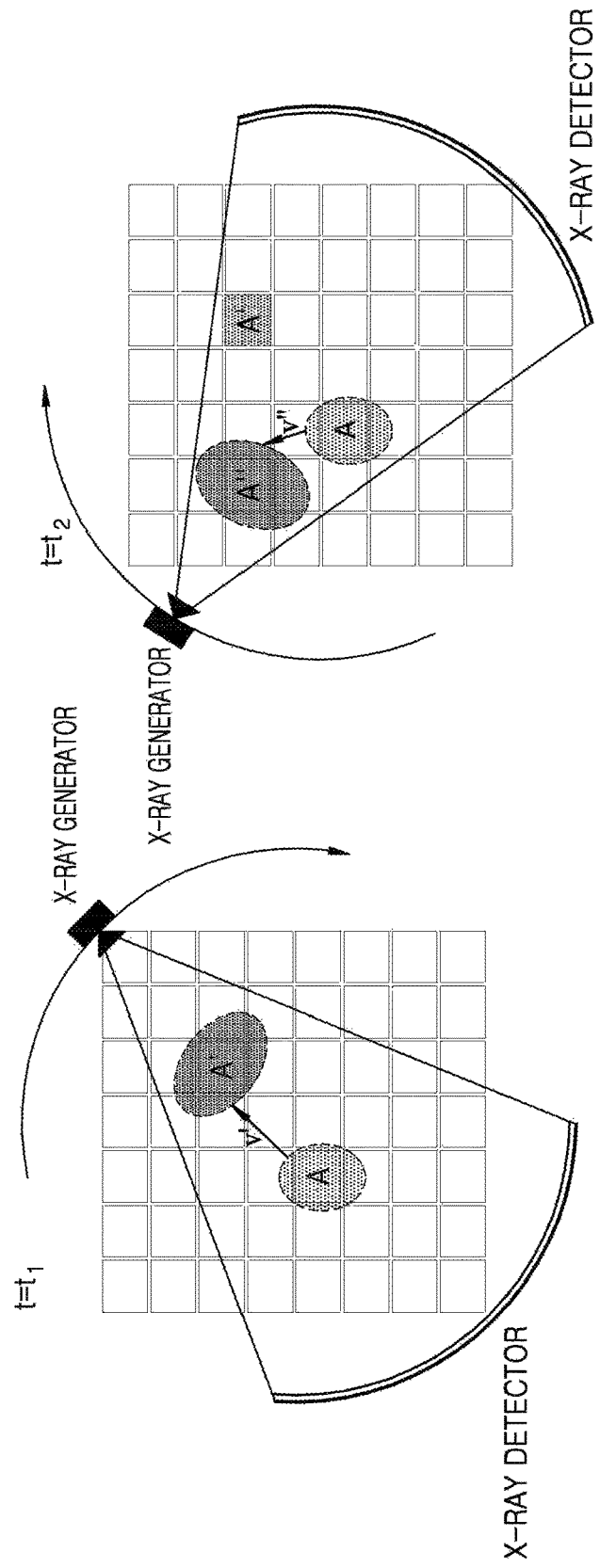
FIG. 7 illustrates a diagram for describing an operation of correcting a location of a voxel by using a tomography apparatus, according to an exemplary embodiment.

FIG. 7 illustrates a diagram for describing an operation of correcting locations of voxels by using a tomography apparatus, according to an exemplary embodiment.

For example, referring to FIG. 7, an object may be at location A when image capturing starts. However, the object may move over time, and at a predetermined time point t1, a real location of the object may be location A'. In addition, at a predetermined time point t2, a real location of the object may be location A". If deblurring is performed based on a PSF corresponding to location A instead of location A' or A", which is the real location of the object, an inaccurate PSF may be applied and deblurring may not be performed properly. Accordingly, the tomography apparatus may predict a motion of the object over time, and correct a real location of the object at a predetermined time point by considering the predicted motion. For example, as illustrated in FIG. 7, the tomography apparatus may correct a location of the object based on a motion vector representing position changes from location A to location A' or a motion vector representing position changes from location A to location A". The tomography apparatus may calculate a motion vector that changes over time, in advance, and store the motion vector. Accordingly, the tomography apparatus may reduce a period of time needed for reconstructing a tomography image. In addition, by performing deblurring the plurality of raw data by applying a PSF corresponding to the corrected location, the tomography apparatus may increase a resolution of the tomography image.

Figure 8:
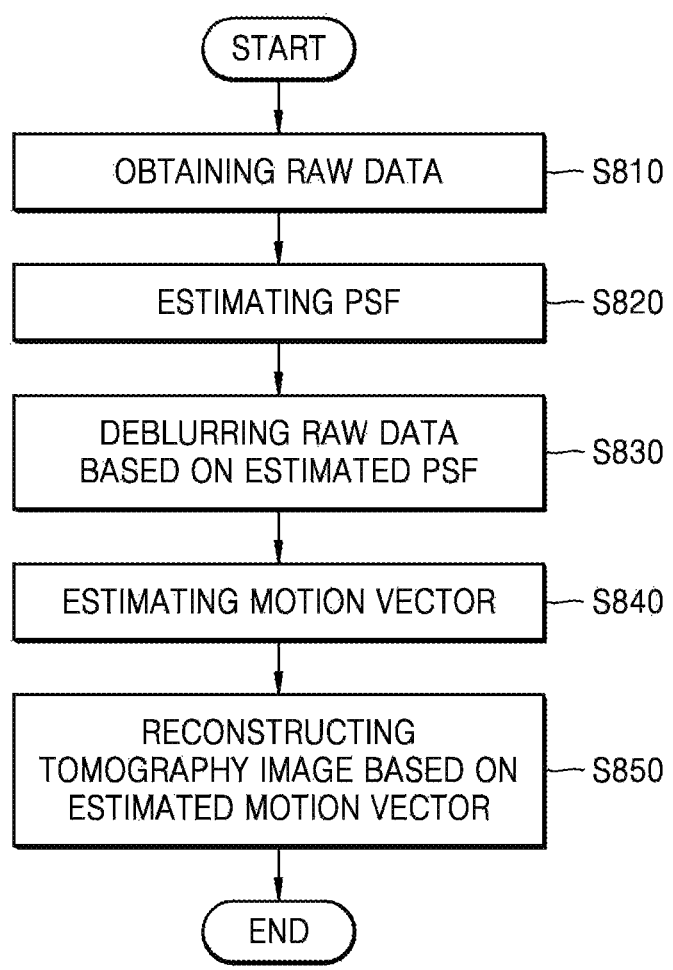
FIG. 8 illustrates a flowchart of a method of reconstructing a tomography image, according to an exemplary embodiment.

FIG. 8 illustrates a flowchart of a method of reconstructing a tomography image, according to an exemplary embodiment.

In operation S810, the tomography apparatus may obtain a plurality of raw data respectively corresponding to a plurality of views by performing a tomography scan on an object. Here, blurring artifacts may occur due to a limitation in performance of the tomography apparatus. The blurring artifacts may degrade an accuracy in reading and diagnosing diseases when a user reads a tomography image to diagnose diseases.

In operation S820, the tomography apparatus may estimate a PSF.

In operation S830, the tomography apparatus may deblur the plurality of raw data based on the PSF. The PSF may vary according to locations in a FOV formed in a gantry. The tomography apparatus may apply an accurate PSF corresponding to each of the locations by deblurring the plurality of raw data based on the PSF that varies according to the locations in the field of view formed in the gantry.

In operation S840, the tomography apparatus may estimate a motion vector corresponding to each time point. The tomography apparatus may improve motion artifacts caused due to a motion of the object, based on a motion vector. The motion of the object is different over time, and thus, a motion vector indicating the motion of the object also varies with time.

In operation S850, the tomography apparatus may apply a motion vector corresponding to the calculated time point, thereby reconstructing an tomography image including corrected object motion.

In addition, according to an exemplary embodiment, the tomography apparatus may calculate time points respectively corresponding to a plurality of views based on the plurality of raw data corresponding to the plurality of views. The tomography apparatus may correct locations of all voxels that construct a field of view formed in a gantry based on motion vectors respectively corresponding to the time points. In addition, the tomography apparatus may perform deblurring the plurality of raw data based on the PSF corresponding to the corrected locations of the voxels.

Accordingly, the tomography apparatus may reconstruct a tomography image having improved blurring artifacts and motion artifacts.

Figure 9A:
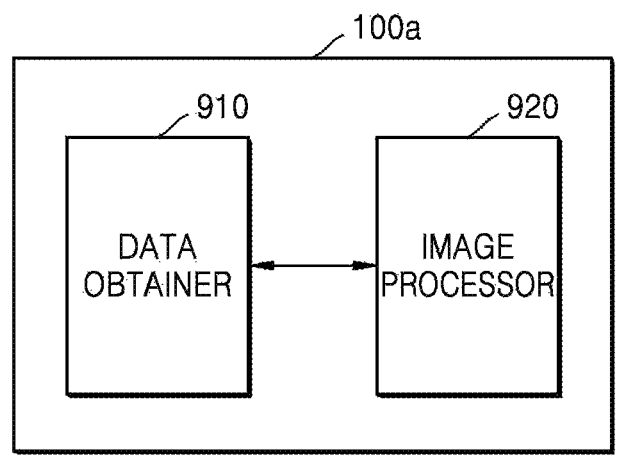
FIGS. 9A and 9B illustrate structural block diagrams of a tomography apparatus according to exemplary embodiments.
Figure 9B:
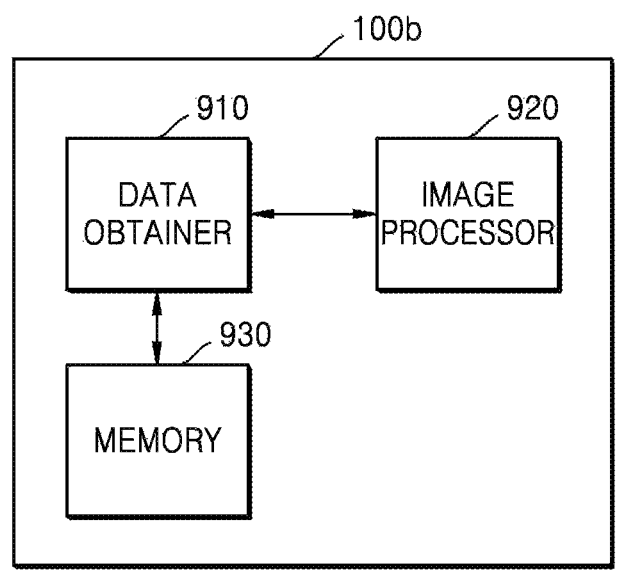

FIGS. 9A and 9B illustrate structural block diagrams illustrating tomography apparatuses 100A and 100B according to an exemplary embodiment.

Referring to FIG. 9A, the tomography apparatus 100A includes a data obtainer 910 and an image processor 920.

The tomography apparatus 100A may be included in the CT system 100 described with reference to FIGS. 1 and 2. In addition, the tomography apparatus 100A may be included in the medical apparatus 136 or the portable device 138 described with reference to FIG. 3 to operate in connection with the CT system 100. In detail, the tomography apparatus 100A may be all medical imaging apparatuses that reconstruct an image based on data acquired using rays that have transmitted through an object. That is, the tomography apparatus 100A may be all medical imaging apparatuses reconstructing a tomography image based on projection data acquired using rays that have transmitted through an object. In detail, the tomography apparatus 100A may be a CT apparatus, an OCT apparatus, or a PET-CT apparatus. Thus, a tomography image acquired using the tomography apparatus 100A according to the exemplary embodiment may be a CT image, an OCT image or a PET image. A CT image is exemplified here as a tomography image. In addition, when the tomography apparatus 100A is included in the CT system 100 described with reference to FIGS. 1 and 2, the data obtainer 910 and the image processor 920 illustrated in FIG. 9A may be respectively included in the gantry 102 and the image processor 126 illustrated in FIG. 2. Accordingly, description already provided with reference to FIGS. 1 and 2 with regard to the tomography apparatus 100A will be omitted below.

The data obtainer 910 obtains a plurality of raw data respectively corresponding to a plurality of views by performing a tomography scan on an object.

The image processor 920 deblurs the plurality of raw data obtained using the data obtainer 910 based on a PSF varying according to locations in a field of view formed in a gantry. For example, the image processor 920 may deconvolute the plurality of raw data obtained using the data obtainer 910 based on a PSF varying according to locations in a field of view.

As described above, a PSF may vary according to locations in a field of view formed in a gantry. If the plurality of raw data is deblurred based on a single PSF in every location in a FOV, an inaccurate PSF may be applied to some locations. Accordingly, the tomography apparatus 100A may deblur raw data based on a PSF varying according to locations in a FOV formed in a gantry, thereby applying accurate PSFs respectively corresponding to respective locations.

In addition, the image processor 920 reconstructs a final tomography image in which a motion of the object is corrected from the plurality of deblurred raw data based on a motion vector indicating an amount of the motion of the object.

The image processor 920 may calculate a motion vector in advance and store the motion vector in a memory. Then the tomography apparatus 100A may correct a motion of the object based on the motion vector stored in the memory.

Alternatively, according to an exemplary embodiment, the image processor 920 may perform deblurring based on a PSF and motion correction based on a motion vector with respect to each of voxels that construct a field of view formed in a gantry. In detail, the image processor 920 may calculate time points respectively corresponding to the plurality of views, and correct locations of the voxels based on a motion vector corresponding to each time point. The object may move while imaging is taking place as described above, and a real location of the object may vary over time.

In addition, the image processor 920 may estimate a PSF corresponding to the respective views and varying according to locations in a field of view formed in a gantry, based on the plurality of raw data respectively corresponding to the plurality of views. Accordingly, the image processor 920 may correct locations of voxels by considering a real location of the object at a predetermined time point, and perform deblurring the plurality of raw data based on a PSF corresponding to the corrected locations of the voxels. In addition, the image processor 920 may reconstruct a final tomography image based on the plurality of deblurred raw data.

In addition, as illustrated in FIG. 9B, the tomography apparatus 100B may further include a memory 930 in addition to the data obtainer 910 and the image processor 920.

The memory 930 may calculate a motion vector varying over time, in advance, and store the motion vector. In addition, the memory 930 may store temporary data or system parameters used in an operation of performing a tomography scan on an object.

The exemplary embodiments can be written as computer programs and can be implemented in general-use digital computers that execute the programs using a transitory or non-transitory computer readable recording medium.

Examples of the computer readable recording medium include magnetic storage media (e.g., ROM, floppy disks, hard disks, etc.), optical recording media (e.g., CD-ROMs, or DVDs), etc.

It should be understood that embodiments described herein should be considered in a descriptive sense only and not for purposes of limitation. Descriptions of features or aspects within each embodiment should typically be considered as available for other similar features or aspects in other embodiments.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. A method of reconstructing a tomography image, the method comprising:
   obtaining a plurality of raw data corresponding to a plurality of views by performing a tomography scan on an object;
   deblurring the plurality of raw data, based on a point spread function (PSF) that varies according to locations in a field of view (FOV) in a gantry; and
   reconstructing a final tomography image in which a motion of the object is corrected from the plurality of deblurred raw data based on a motion vector indicating the motion of the object.

2. The method of claim 1, wherein the deblurring comprises deconvoluting the plurality of raw data based on the PSF that varies according to the locations in the FOV in the gantry.

3. The method of claim 1, further comprising:
   obtaining a plurality of partial images by using the plurality of raw data corresponding to the plurality of views obtained by performing a tomography scan on the object;
   measuring a motion of the object based on the plurality of partial images; and
   representing the measured motion of the object as the motion vector.

4. The method of claim 1, further comprising estimating a PSF that varies according to the locations in the FOV in the gantry corresponding to the plurality of views based on the plurality of raw data.

5. A tomography apparatus comprising:
   a data obtainer configured to obtain a plurality of raw data corresponding to a plurality of views by performing a tomography scan on an object; and
   an image processor configured to:
      deblur the plurality of raw data based on a point spread function (PSF) varying according to locations in a field of view (FOV) in a gantry; and
      reconstruct a final tomography image in which a motion of the object is corrected from the plurality of deblurred raw data based on a motion vector indicating the motion of the object.

6. The tomography apparatus of claim 5, wherein the image processor deconvolutes the plurality of raw data based on the PSF varying according to the locations in the FOV in the gantry.

7. The tomography apparatus of claim 5, wherein the data obtainer obtains a plurality of partial images by using the plurality of raw data corresponding to the plurality of views obtained by performing a tomography scan on an object,
   wherein the image processor measures a motion of the object based on the plurality of partial images and represents the measured motion of the object as the motion vector.

8. The tomography apparatus of claim 5, wherein the image processor estimates a PSF corresponding to the plurality of views and varying according to the locations in the FOV in the gantry based on the plurality of raw data.

9. A tomography apparatus comprising:
   a data obtainer configured to obtain a plurality of raw data respectively corresponding to a plurality of views by performing a tomography scan on an object; and
   an image processor configured to calculate time points respectively corresponding to the plurality of views and correct locations of all voxels that construct a field of view (FOV) in a gantry, based on a motion vector corresponding to each of the time points, and deblur the plurality of raw data based on a point spread function (PSF) corresponding to the corrected locations of the voxels.

10. The tomography apparatus of claim 9, wherein the image processor estimates the PSF corresponding to locations of the voxels based on angles corresponding to the views and the corrected locations of the voxels.

11. The tomography apparatus of claim 9, wherein the image processor calculates projection coordinates corresponding to the corrected locations of the voxels, and deconvolutes the projection coordinates based on the PSF corresponding to the corrected locations of the voxels.

12. The tomography apparatus of claim 9, further comprising a memory,
   wherein the image processor predicts in advance a motion in each voxel with respect to time points respectively corresponding to the plurality of views, and representing the predicted motion as each of the motion vectors, wherein the memory stores each of the motion vectors.

13. The tomography apparatus of claim 9, wherein the image processor reconstructs a final tomography image based on the plurality of deblurred raw data.

* * * * *